United States Patent [19]

Schumacher et al.

[11] Patent Number: 5,219,866
[45] Date of Patent: Jun. 15, 1993

[54] OCTADECYL-[2-(N-METHYLPIPERIDINO)-ETHYL]-PHOSPHATE AND A PROCESS FOR ITS PREPARATION

[75] Inventors: Wolfgang Schumacher, Langen; Jürgen Engel, Alzenau; Gerhard Nössner, Offenbach; Bernhard Kutscher, Maintal; Jurij Stekar; Peter Hilgard, both of Bielefeld, all of Fed. Rep. of Germany

[73] Assignee: Asta Medica AG, Fed. Rep. of Germany

[21] Appl. No.: 907,025

[22] Filed: Jul. 1, 1992

[30] Foreign Application Priority Data

Jul. 4, 1991 [DE] Fed. Rep. of Germany ....... 4122140
Sep. 4, 1991 [DE] Fed. Rep. of Germany ....... 4129364

[51] Int. Cl.$^5$ .................. A61K 31/445; C07F 9/02
[52] U.S. Cl. ...................................... 514/315; 546/22
[58] Field of Search .......................... 546/22; 514/315

[56] References Cited

U.S. PATENT DOCUMENTS 4,935,520  6/1990  Nojima et al. ................... 546/22

FOREIGN PATENT DOCUMENTS 0108565 10/1983 European Pat. Off. .
288868   5/1973  U.S.S.R. .
301951   5/1973  U.S.S.R. .

Primary Examiner—C. Warren Ivy
Assistant Examiner—Celia Chang
Attorney, Agent, or Firm—Cushman, Darby & Cushman

[57] ABSTRACT

Octadecyl-[2-(N-methylpiperidino)-ethyl]-phosphate and a process for its preparation. This compound is useful for the treatment of cancer.

2 Claims, No Drawings

OCTADECYL-[2-(N-METHYLPIPERIDINO)-ETHYL]-PHOSPHATE AND A PROCESS FOR ITS PREPARATION

The present invention relates to octadecyl-[2-(N-methyl-piperidino)-ethyl]-phosphate, a processes for its preparation and medications containing this compound as active ingredient.

BACKGROUND OF THE INVENTION

Published European Patent Application 108,565 relates to compounds of general formula

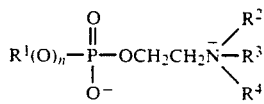

and their pharmaceutically acceptable salts where $R^1$ is an aliphatic hydrocarbon radical with 8-30 carbon atoms, the radicals $R^2$, $R^3$ and $R^4$ are the same or different and are hydrogen or lower alkyl radicals or where the group $NR^2R^3R^4$ represents a cyclic ammonium group and n has the values 0 or 1. These compounds are said to have an anti-tumor effect and a fungus-inhibiting effect.

SUMMARY OF THE INVENTION

In accordance with the present invention, it has been / found that octadecyl-[2-(N-methyl-piperidino)-ethyl]-phosphate surprisingly has a very much better or more advantageous anti tumor effect than the compounds described or mentioned in European application 108,565. In addition, it has been found that this compound causes inhibition of blood platelet aggregation and, in addition, has a phospholipase-$A_2$-inhibiting and lipoxygenase-inhibiting effect.

The invention also relates to a new, improved method of preparation and working up of octadecyl-[2-(N-methyl-piperidino)-ethyl]-phosphate (process a).

It has surprisingly been found that the process of the invention achieves a higher total yield and a purer product, although one less purification step is used than in the previously known process for producing alkylphosphocholines. What is more, less solvent is used in this process. The new process of the invention also avoids the use of alkylating reagents such as dimethyl sulphate which lead, through the use of potassium carbonate as an auxiliary base, to an excessively high potassium content of the product. The potassium content must be kept as low as possible in substances used as pharmaceutical active substances. In addition the time-consuming chromatography step is no longer needed for purification purposes.

The product purity achieved according to the new process is higher than in the known process for the preparation of alkylphosphocholines, and in addition it produces higher yields (in particular in larger-scale preparation).

The first step of process a) consists in reacting phosphorus oxychloride with N-octadecyl alcohol in halogenated hydrocarbons, saturated cyclic ethers, acyclic ethers, saturated hydrocarbons with 5 to 10 carbon atoms, liquid aromatic hydrocarbons which may also be substituted by halogen (in particular chlorine) or in mixtures of the above mentioned solvents or without solvents, optionally in the presence of a basic substance conventionally used for this purpose.

Halogenated hydrocarbons that may for example be used are hydrocarbons containing 1 to 6 carbon atoms where one or several or all hydrogen atoms are replaced by chlorine atoms. It is for example possible to use methylene chloride, chloroform, ethylene chloride, chlorobenzene or dichlorobenzene. If a halogen-substituted aromatic hydrocarbon is used, it preferably is substituted with one or two halogen atoms.

Saturated cyclic ethers that may be used are for example ethers with a ring size of 5-6 which consists of carbon atoms and one or two oxygen atoms. Examples of such solvents are tetrahydrofuran and dioxane.

The acyclic ethers consist of 2 to 8 carbon atoms and are liquid. The following may for example be used: diethyl ether, diisobutyl ether, methyl-tert.-butyl ether, diisopropyl ether.

Saturated hydrocarbons that may be considered are unbranched and branched hydrocarbons which consist of 5 to 10 carbon atoms and are liquid. Pentane, hexane, heptane, cyclohexane may for example be considered.

Aromatic hydrocarbons that may for example be considered are benzene and alkyl-substituted benzenes, where the alkyl substituents contain 1 to 5 carbon atoms.

Basic substances that may be considered both for the reaction of phosphorus oxychloride with the n-octadecyl alcohol and also for the subsequent reaction with the n-methyl-piperidino-ethanol salt are amines, for example aliphatic amines of formula $NR_1R_2R_3$, where $R_1$, $R_2$ and $R_3$ are the same or different and represent hydrogen or $C_1$-$C_6$-alkyl or also aromatic amines such as pyridine, picoline, quinoline.

For the reaction with the N-methyl-piperidino-ethanol salt, it is possible to add the basic substance required for that purpose at the same time, or alternatively before, the N-methyl-piperidino-ethanol salt. For this reaction a solvent is needed in any case; in other words if the first reaction step is conducted without a solvent, one has to be added at this stage. The molar ratio of phosphorus oxychloride to the octadecyl alcohol is for example between 1.5:1 and 1:1.

The N-methyl-piperidino-ethanol salt is for example used in excess in relation to the n-octadecyl alcohol (about 1.1-1.5 molar excess).

If the reaction of the phosphorous oxychloride with the n-octadecyl alcohol occurs in the presence of a basic substance, the amount of the basic substance is for example 1 to 3 moles for each mole of $POCl_3$. For the subsequent reaction with the piperidine salt[1], the amount of basic substance used is for example 1 to 5 Mol related to 1 Mol alkanol.

[1] In this specification "salt" always means N-methylpiperidino-ethanol salt.

The reaction temperature of the reaction of phosphorus oxychloride with n-octadecyl alcohol is between $-30°$ C. and $+30°$ C., preferably between $-15°$ C. and $+5°$ C., in particular between $-10°$ C. and $-5°$ C.

The reaction time of this reaction is for example 0.5-5 hours, preferably 1-3 hours, in particular 1.5-2 hours. If the reaction occurs in the presence of a basic substance, it generally takes place quickly (about 33 minutes).

The piperidine salt is then added in portions or completely. Salts of N-methyl-piperidine-ethanol that may be considered are salts with mineral acids, (such as sulphuric acid, hydrochloric acid) as well as salts with organic acids such as acetic acid, para-toluenesulphonic acid and the like.

This reaction step occurs in an inert solvent. Solvents that may be used in this step are the same as are used for the reaction of the phosphorus oxychloride with the n-octadecyl alcohol, if this reaction occurs in a solvent.

The basic substance is then dissolved in one of the stated solvents, or a solvent is added dropwise. Solvents for the basic substance that are preferably used are: halogenated hydrocarbons, saturated cyclic ethers, acyclic ethers, saturated hydrocarbons with 5 to 10 carbon atoms, liquid aromatic hydrocarbons or mixtures of the above mentioned solvents. These are the same solvents that may be used for the reaction of the phosphorus oxychloride with the n-octadecyl alcohol.

Addition of the basic substance causes the temperature to rise. Care should be taken to ensure that the temperature is maintained in a range between 0° C. and 40° C., preferably 10° C. to 30° C., in particular to 15° C. to 20° C. The reaction mixture is then stirred at 5° C. to 30° C., preferably 15° C. and 25° C. (for example 1 hour to 40 hours, preferably 3 hours to 15 hours).

The reaction batch is hydrolyzed by addition of water. It is necessary in this step to maintain a temperature between 10° C. and 30° C., preferably 15° C. and 30° C., in particular between 15° C. and 20° C.

The previously mentioned hydrolysis liquids may also contain basic substances. Basic substances of this kind that may be considered are carbonates and hydrogen carbonates of alkali and alkaline earth metals.

To complete the hydrolysis, the mixture is then stirred for a further 0.5 hours to 4 hours, preferably 1 to 3 hours, in particular 1.5 to 2.5 hours at 10° C. to 30° C., preferably at 15° C. to 25° C., in particular at 18° C. to 22° C.

The reaction solution is then washed with a mixture of water and alcohols (preferably aliphatically saturated alcohols with 1 to 4 carbon atoms) which may optionally also contain a basic substance. The mixing ratio water:alcohol may for example be between 5 and 0.5, preferably 1-3 (V/V). Basic substances for the washing liquid that may for example be considered are carbonates and hydrogen carbonates of alkali and alkaline earth metals as well as ammonia (for example aqueous ammonia). A 3% sodium carbonate solution in water is particularly preferred.

It is subsequently optionally possible to wash the reaction solution with an acid solution. Acid washing is advantageous to remove unreacted basic constituents of the reaction solution, particularly when methylene chloride is used as solvent.

The washing solution consists of a mixture of water and alcohols. Mixtures of aliphatically saturated alcohols which contain 1 to 4 carbon atoms are preferably used, it optionally also being possible for an acid substance to be present. The mixing ratio water:alcohol may for example be between 5 and 0.5, preferably 1-3 (V/V).

Acid substances that may for example be used as the washing liquid are for example mineral acids and organic acids, for example hydrochloric acid, sulphuric acid or tartaric acid, and citric acid. A 10% solution of hydrochloric acid in water is particularly preferred.

The mixture is then washed once more with a mixture of water and alcohols. Mixtures of aliphatically saturated alcohols which contain 1 to 4 carbon atoms are preferably used. Optionally, it is possible for a basic substance also to be present.

The mixing ratio water:alcohol may for example be between 5 and 0.5, preferably 1-3.

The washed phases are then combined and dried in the conventional manner and then the solvent is removed (preferably under reduced pressure, for example 5 to 100 mbar) optionally after addition of 150-1000 ml, preferably 300-700 ml, in particular 450-550 ml of an aliphatic alcohol (for each molar part by weight of dried product). The alcohols that may advantageously be considered are saturated aliphatic alcohols having a chain length of 1 to 5 carbon atoms. This alcohol treatment is designed to remove residual water completely.

The product obtained in this manner may be purified in the conventional way (e.g. by chromatography, recrystallization).

The following, also inventive, purification process is, however, particularly preferred:

The solid residue as described above is for example suspended in saturated aliphatic ketones (3-6 carbon atoms), for example acetone, butatone, methyl-tert.-butyl ketone, stirred for 1 to 4 hours, preferably 2 hours, suction filtered and dried at 20° C. to 50° C. in a vacuum at 5 Torr to 100 Torr.

The product which has been pre-purified in this manner is taken up in anhydrous alcohols ($C_1$ to $C_4$) or in alcohols containing a maximum of 5 % by weight of water at 20° C. to 60° C., preferably 40° C. and insoluble constituents are filtered off. Alcohols that may for example be used are methanol, ethanol, isopropanol, butanol, isobutanol. The filtrate obtained is then stirred with a mixed-bed ion exchanger, for example Amberlite ® MB3 for example for 1 to 5 hours, preferably 2 hours, at 10° C. to 50° C., preferably 20° C.

Instead of a mixed-bed ion exchanger it is also possible for purification to be effected successively with an acidic ion exchanger and a basic ion exchanger. Ion exchangers that may be used are all insoluble solids that contain ion-exchanging groups.

Acidic ion exchangers are those which contain for example acid groups such as sulphonic acid groups, carboxyl groups. Examples are ion exchangers with sulphonic acid groups in a polystyrene matrix such as Amberlite ® IR 120, Dowex ® HCR, Duolite ® C 20 or Lewatit ® S 100. Weakly acidic ion exchangers are for example those base on a polyacrylic acid matrix, such as Amberlite ® IRC 76, Duolite ® C 433 or Relite ® CC.

Basic ion exchangers that may for example be considered are those having on a polymer matrix (e.g. polystyrene matrix) primary, secondary, tertiary or quaternary amino groups such as Duolite ® A 101, Duolite ® A 102, Duolite ® 15 A 348, Duolite ® A 365, Duolite ® A 375, Amberlite ® IRA 67, Duolite ® A 375, Amberlite ® IRA 458 and Duolite ® A 132.

Mixed-bed ion exchangers are mixtures of acid and alkaline ion exchanger resins, such as Amberlite ® MB1, Amberlite ® MB2, Amberlite ® MB3 and Amberlite ® MB6.

Other ion exchangers that may be used are listed in Ullmann's Encyclopedia of Industrial Chemistry, 5th Edition (1989), Volume A14, p. 450.

Following suction filtering of the ion exchanger resin, the mixture is evaporated under reduced pressure (for example 20 Torr to 200 Torr) at 40° C. to 70° C., and the mixture is then recrystallized from halogenated hydrocarbons, saturated aliphatic ketones or from alcohol/ketone mixtures.

Halogenated hydrocarbons that may for example be considered for the recrystallization are hydrocarbons containing 1 to 6 carbon atoms where one or several or all carbon atoms are replaced by chlorine atoms. It is for example possible to use methylene chloride, chloroform, ethylene chloride, chlorobenzene.

Alcohols that may be considered are saturated aliphatic alcohols containing 1 to 6 carbon atoms and 1 to 3 hydroxyl groups. Ketones that may be considered are saturated, aliphatic ketones with 3 to 6 carbon atoms. The mixing ratio alcohol:ketone is 1 to 1-5 (volume/volume). An ethanol/acetone mixture in the ratio of 1:1 (V/V) is specially preferred.

The crystals of octadecyl-[2-(N-methyl-piperidino)ethanol phosphate obtained in this way are suction filtered and, if necessary, washed. For example, the crystals may be washed with saturated hydrocarbons containing 1 to 6 carbon atoms. (Temperature of the washing liquid may be for example 15° to 30° C.).

It is also possible to obtain the compound of the invention by reacting, in known manner
b) a compound of formula

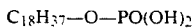

$$C_{18}H_{37}-O-PO(OH)_2 \qquad I$$

or a reactable derivative of this compound with a compound of formula II:

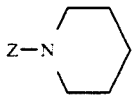

optionally in the presence of basic substances, where Z represents hydrogen, methyl or the group $-CH_2-CH_2-OH$ and the piperidine compound may also be present in the form of the N-methyl-piperidinium derivative, where in this case the positive charge is neutralized by the anion of an inorganic or organic acid and optionally methylated, or c) a compound of the formula II

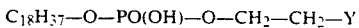

$$C_{18}H_{37}-O-PO(OH)-O-CH_2-CH_2-Y \qquad III$$

where Y is chlorine, bromine or iodine is reacted with piperidine or N-methyl-piperidine and optionally methylated or d) a compound of the general formula IV

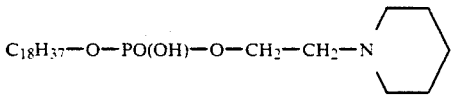

is methylated or a compound obtained according to b) or c) is methylated.

With regard to process b):

The process b) may be carried out without solvent (in this case excess of compound II) or in an inert solvent at temperatures between 0° and 180° C., preferably 18°-120° C. Solvents that are for example suitable are: lower aliphatic alcohols (methanol), aliphatic straight-chain ethers (diethyl ether), saturated cyclic ethers (dioxane, tetrahydrofuran), aromatic hydrocarbons (toluene, benzene, pyridine), chlorinated aliphatic lower molecular hydrocarbons ($CHCl_3$, $CCl_4$), lower alkyl amides or dialkyl amides of lower molecular aliphatic carboxylic acids (dimethyl formamide, dimethyl acetamide) or also dimethyl sulphoxide, acetonitrile. The working up is carried out in known manner by hydrolysis using alcohols/water or water alone. Purification of the reaction product is effected for example by recrystallization or column chromatography. The reaction according to process b) can also be conducted in the presence of additional basic substances such as tertiary amines (N-methyl piperidine, N-methyl morpholine, N-methyl pyrolidine, quinoline, pyridine).

If the starting material is the free acid $C_{18}H_{37}-O-PO(OH)_2$, this is activated by known condensation agents such as 2,4,6-trimethylbenzene sulphonyl chloride, 8-quinoline sulphonyl chloride, 2,4,6-isopropylbenzene sulphonyl imidazolide, 2,4,6-trimethylbenzene sulphonyl tetrazolide or dicyclohexyl carbodiimide and then reacted.

If the starting material $C_{18}H_{37}-O-PO(OH)_2$ is present in the form of an activated derivative, this is for example a compound where both OH groups are substituted by halogen (Cl, Br, I).

The activated derivative used may for example also be a compound of formula

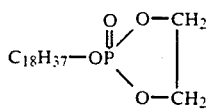

in which case the reaction is preferably carried out in an autoclave or a stirring apparatus at a temperature between $-20°$ C. to 130° C.

If the starting compound of formula II is used as a piperidinium salt, the acid ions that may be considered are: $Cl^-$, $Br^-$, $I^-$, tosylate anion, sulphuric acid anion ($HSO_4^-$, $SO_2^{2-}$).

With regard to process c):

This reaction is conducted in known manner without solvent or in an inert solvent at temperatures between 50° to 100° C. If a solvent is used, the solvents that may be considered are the same as for process b): the piperidine or N-methyl-piperidine may also act in excess as solvent.

The reaction is appropriately carried out in the presence of an acid-binding (halide-binding) substance such as $Ag_2CO_3$.

With regard to process d):

The alkylation is for example conducted by reaction with compounds of formula MHal, $AsSO_2OM$ and $SO_2 2(OM)_2$, where Hal is a halogen atom (in particular chlorine, bromine or iodine), Ar is an aromatic radical (for example a phenyl or naphthyl radical optionally substituted by one or several lower alkyl radicals and M is the methyl radical. Examples are p-toluene sulphonic acid methyl ester, dimethyl sulphate, methyl halides. The alkylation reaction is optionally carried out with addition of a conventional acid-binding agent, such as alkali hydroxides, alkali carbonates, alkali hydrogen carbonates, alkaline earth carbonates, alkali acetates, tertiary amines (for example trialkyl amines such as triethylamine), pyridine or also alkali hydrides at temperatures between 0° and 200° C., preferably 40° and 140° C. in inert solvents or suspension agents. Solvents and dispersing agents that may for example be considered are: aromatic hydrocarbons such as benzene, toluene, xylene; aliphatic ketones such as acetone, methyl ethyl ketone; halogenated hydrocarbons such as chloroform, carbon tetrachloride, chlorobenzene, methylene chloride; aliphatic ethers such as butyl ether; cyclic ethers such as tetrahydrofuran, dioxane; sulphoxides such as dimethyl sulphoxide; tertiary acid amides such as dimethyl formamide, N-methyl pyrrolidone, hexamethylphosphoric acid triamide; aliphatic alcohols such as methanol, ethanol, isopropanol, amyl alcohol, tert.-butanol, cycloaliphatic hydrocarbons such as cyclohexane and the like. It is also possible to use aqueous mixtures of the solvents mentioned. Working is frequently at the reflux temperature of the solvents or dispersing agents used.

The alkylation reaction components are frequently used in excess. The alkylation may also be conducted in the presence of tetraalkyl ammonium salts (in particular the halides) in combination with alkali hydroxides at temperatures between 0°-100° C., preferably 20°-80° C. in an aprotic solvent or also in chloroform or methylene chloride. Aprotic solvents that may in particular be considered are: tertiary amides (dimethyl formamide, N-methyl pyrrolidone, dimethyl sulphoxide, acetonitrile, dimethoxyethane, acetone, tetrahydrofuran.

The alkylation may optionally also be conducted by first preparing an alkali compound (sodium salt, potassium salt or also lithium salt for example) from the compound to be alkylated by reacting it in an inert solvent such as dioxane, dimethyl formamide, benzene or toluene with an alkali metal, alkali hydride or alkali amides (in particular sodium or sodium compounds) or butyl lithium at temperatures between 0° and 150° C. and then adding the alkylation agent.

Instead of the listed alkylating agents it is also possible to use other chemical equivalent agents conventionally used in chemistry (see for example also L. F. and Mary Fieser "Reagents for Organic Synthesis", John Wiley and Sons. In., New York, 1967, Vol. 1, pages 1303–4 and Vol. 2 page 471).

TABLE 1

| Substance | Growth inhibition index WHI in % in vivo/humane KB tumour cell line transplanted into nude mice | $EC_{90}$ in μg/ml Human KB tumour cell line in vitro | Cape-Index |
|---|---|---|---|
| 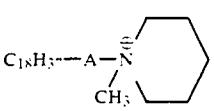 D 20133, compound of the invention | 121 | 0.3 | 403 |
| Compounds of similar structure | | | |
| 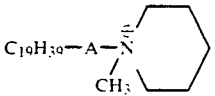 D21545 | 13.7 | 1.3 | 10 |
| 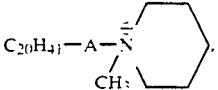 D 21033 | 7 | 0.3 | 23 |
| 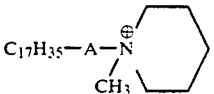 D 21052 | 0 | 3.2 | 0 |
| 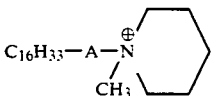 D 20813 | 76 | 2 | 38 |
| 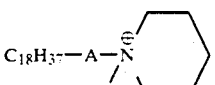 D 20317 | 38 | 1,4 | 27 |
| 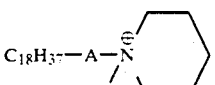 D 20110 | 25 | 1 | 25 |

TABLE 1-continued

| Substance | Growth inhibition index WHI in % in vivo/humane KB tumour cell line transplanted into nude mice | $EC_{90}$ in μg/ml Human KB tumour cell line in vitro | Cape-Index |
|---|---|---|---|
| 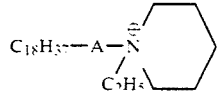 D 20931 | 13 | 1 | 13 |
| 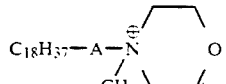 D 20680 | 0 | >10 | 0 |
| 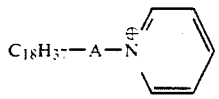 D 19862 | 0 | >1 | 0 |
| $C_{18}H_{37}-A-\overset{+}{N}(CH_3)_3$ D 19391 | 11 | 0.31 | 36 |
| 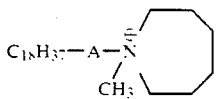 D20918 | 0 | 1 | 0 |
| 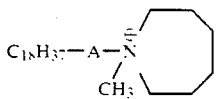 D 20706 | 0 | 3.1 | 0 |
| 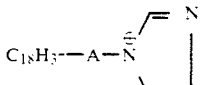 D 20745 | 20 | 10 | 2 |

$A = O-PO-O-CH_2-CH_2-$
        $|$
        $O^-$

The growth inhibition index WHI is determined in the human KB tumor cell line which is transplanted in nude mice. The growth inhibition index is defined as follows:

$$WHI = \frac{M_{control} - M_{treatment}}{M_{control}} \times 100\%$$

of the treated group or in the control group on the 14th day after treatment related to the value on the day of application. A WHI greater than 100% means that the tumors have become smaller due to the treatment; a WHI smaller than 100%, in contrast, only shows a treatment-related slowing down in tumor growth as compared to the controls. In other words, the higher the WHI, the stronger the antitumor efficacy of a test substance.

The $EC_{90}$ is determined in vitro in the same cell line. The $EC_{90}$ is the concentration of substance having an antitumor effect in μg/ml which inhibits the growth of cancer cells in vitro by 90% in comparison to a control experiment without addition of the antitumor-acting substance.

The Cape Index (coefficient for cancer-inhibiting effects) is a measure for the high selectivity and specificity of a chemical substance vis-à-vis antitumor-acting substances. This Cape index is obtained by dividing the WHI index by the $EC_{90}$ index.

This means that an effect in the animal (in vivo) is compared to the effect in an in vitro system. It has been found that the higher the coefficient formed in this manner, the more selective and effective the antitumor effect of a substance is.

The compounds of the invention display a good antineoplastic effect in the KB tumor (human carcinoma of the buccal cavity, transplanted subcutaneously to nude mice) and in autochthonous, chemically-induced DMBA-breast gland cancer in the rat.

For example a dose of 2×316 mg/kg body weight of the compound of the invention, given at intervals of one week, achieved a regression of the KB tumors.

After a 14-day oral treatment with an oral dose of 21.5 mg/kg body weight of the compound of the invention daily, DMBA tumors weighing 5 g regressed to the borderline of palpability.

As shown in Table 1, the compound of the invention therefore has an antitumor efficacy that is higher and more specific by a multiple factor as compared to the compounds of similar structure. This effect was not obvious.

DETAILED DESCRIPTION OF PREFERRED EMBODIMENTS

EXAMPLE 1

Preparation according to the new process (process a)
Octadecyl-[2-(N-methylpiperidino)-ethyl]-phosphate (number D-20133)

9.2 ml (0.1 Mol) $POCl_3$ in 50 ml chloroform are added to a stirring apparatus under nitrogen and cooled in an ice bath to 5° C. 24.3 g (0.09 Mol) octadecanol are dissolved in 100 ml chloroform under light heating and added dropwise together with 32 ml (0.40 Mol) pyridine at a temperature of 5°-12° C. Dropping time: 30 minutes. After post-stirring for half an hour 37.9 (0.12 Mol) solid 2-(N-methyl-piperidino)-ethanol tosylate are added and then 40 ml pyridine are added dropwise. This causes the temperature to rise to 15° C. The ice bath is removed and the reaction mixture is stirred for 2.5 hours at room temperature. For purposes of hydrolysis 15 ml water are added dropwise within 10 minutes. After stirring for half an hour, the reaction solution is washed in each case once with 200 ml water/methanol (1:1), 200 ml 3 percent $Na_2CO_3$/methanol (1:1) and 200 ml water/methanol (1:1). The reaction solution washed in this manner is dried over $Na_2SO_4$ and evaporated in a rotary evaporator in a vacuum after addition of a little i-propanol.

The residue is recrystallized from 200 ml butanone. The wax-like product formed is filtered off and dissolved with heat in 150 ml 96% ethanol. The precipitate is filtered off and the filtrate is cooled in the refrigerator for four hours.

The precipitate is filtered off again and the filtrate mixed with 85 g Amberlite ® MB3 After stirring for three hours, the ion exchanger is removed and the solution evaporated in a rotary evaporator in a vacuum. The residue is recrystallized from 150 ml butanone followed by drying in a vacuum over phosphorus pentoxide.

Yield: 21.7 g (45.6 mmol, 51%).
MP 113° C.
Rf-value: 0.53 (thin layer chromatogram in silica gel, mobile phase methylene chloride/methanol/25 percent ammonia 80:25:5.

The starting -N-methyl-piperidino compound may for example be prepared in the following manner:

64.59 g (0.50 mol) 2-piperidinoethanol are dissolved in 125 ml acetonitrile and mixed dropwise with cooling with a solution of 93.1 g (0.50 mol) 4-toluene sulphonic acid methyl ester in 125 ml acetonitrile within 30 minutes. The mixture is stirred for half an hour each at room temperature and under reflux. After cooling, the solvent is removed in a vacuum and the residual oil is dissolved in 200 ml hot acetone. The product precipitates in crystalline form on cooling. The crystallization is completed in a refrigerator. After suction filtering, the product is post-washed with acetone and dried at 40° C. over $P_2O_5$ in a vacuum.

Yield: 139 g (0.45 mol, 90%) 2-hydroxyethyl-N-methyl piperidinium tosylate.

EXAMPLE 2

Preparation according to process c)
Octadecyl-[2-(N-methyl piperidino)-ethyl]-phosphate (number D-20133)

20.0 g (44.0 ml) octadecyl-2-bromoethyl phosphate and 73 ml (600 mmol) N-methyl piperidine are heated under reflux for 3 hours. After cooling the product is evaporated, the residue taken up in 120 ml methanol and boiled for three hours under reflux after addition of 17.9 g (62.0 mmol) $Ag_2CO_3$. The reaction mixture is filtered hot over a membrane filter and concentrated. The residue is dissolved in 25 ml $CHCl_3$/methanol/25 percent $NH_4OH$ (80:25:5) and filtered over a layer of silica gel. The filtrate is evaporated, the residue is stirred with acetone and suction filtered. The product is dissolved in a little $CH_2Cl_2$ and precipitated with acetone.

Yield: 3.50 g (7.38 mmol, 17%) white powder.
MP: 110°-112° C.
Rf-value: 0.53, thin layer chromatogram in silica gel, mobile phase/methanol/25% ammonia 80:25:5. Preparation of the starting material: Octadecyl-2-bromoethyl-phosphate: 62.5 g (0.50 mol) 2-bromoethanol are dissolved in 50 ml $CHCl_3$ and mixed dropwise at room temperature with 68.7 ml (0.75 mol) $POCl_3$. The mixture is heated under argon for 6 hours to 55° C. and then left to stand over night. The result is then evaporated in a vacuum and the 2-bromoethylphosphorous oxydichloride formed is distilled in a high vacuum.

Yield: 68.0 g (281 mmol; 57%) 2-bromoethylphosphorous oxydichloride, boiling point 58°-62° C. (0.1 mbar).

44.4 g (0.164 mol) octadecanol and 60 g (0.249 mol) 2-bromoethylphosphorous oxydichloride are dissolved in 250 ml toluene and mixed dropwise with stirring with 19.8 ml (0.249 mol) pyridine. After stirring for 4 hours the mixture is evaporated, the residue mixed with 160 ml $H_2O$ and heated under reflux for 1.5 hours. The still hot suspension is poured onto 160 g ice to which 41.5 ml concentrated HCl had been added. The precipitating octadecyl-2-bromoethylphosphate is suction filtered and dried over $P_2O_5$.

Yield: 64.5 g (0.140 mmol, 86%) octadecyl-2-bromoethylphosphate.

EXAMPLE 3

Preparation of octadecyl-[2-(N-methylpiperidino-ethyl]-phosphate according to process b)

Ethyleneoctadecylphosphate is dissolved in 600 ml acetonitrile and caused to react in an autoclave for 24 hours with 125 ml (1.03 mol) N-methylpiperidine at 80° C. After cooling the apparatus is opened and the brown reaction solution is placed in a refrigerator for crystallization purposes. After suction filtering and drying, 92 g (193 mmol, 61%) of reaction product are obtained. The crystals are stirred with acetone, dissolved in $CH_2Cl_2$ and chromatographed in silica gel with $CHCl_3$/methanol/25 percent $NH_4OH$ (60:40:4, then 80:25:5). The fractions containing the product are concentrated, the octadecyl-[2-N-methylpiperidino)-ethyl]-phosphate precipitating as a white solid after drying over $P_2O_5$ in a vacuum.

MP: 108°–110° C.

Rf: 0.53, thin layer chromatogram on silica gel; mobile phase methylene chloride/methanol/25% aqueous ammonia 80:25:5

Yield: 18 g (37.8 mmol, 12%)

The starting ethylene octadecyl phosphate is obtained for example as follows in this example:

85.3 G (315 mmol) octadecanol are dissolved under $N_2$ in a dry stirring apparatus in 500 ml dry ether and mixed with 41 ml (345 mmol) freshly distilled N-methylpiperidine. After cooling to 5° C. a solution composed of 50 g (345 mmol) 2-chloro-2-oxo-1,3,2-dioxaphospholan in 170 ml dry ether at 5°–10° C. is added dropwise with exclusion of moisture within 30 minutes. When addition is completed, the mixture is stirred at room temperature for one hour. The precipitated N-methylpiperidinium hydrochloride is suction filtered under a protecting gas and the filtrate is concentrated in a vacuum at a bath temperature of 30° C. Yield: 103 g (284 mmol, 90%) ethyleneoxtadecyl phosphate.

EXAMPLE 4

Preparation of octadecyl-[2-(N-methylpiperidino)-ethyl]-phosphate according to process d), methylation.

3.7 g (8.00 mmol) octadecyl-2-piperidinoethylphosphate and 0.63 ml (10.0 mmol) methyliodide are dissolved in 20 ml acetonitrile and heated in an autoclave for 6 hours to 100° C. The mixture is cooled to room temperature, the resultant precipitate is suction filtered, dissolved in 140 ml 96 percent ethanol and stirred for 1.5 hours with 50 mg ion exchanger Amberlite ® MB3 The mixture is evaporated after the ion exchanger has been filtered off. The residue is stirred with 20 ml butanone and dried in a vacuum at 40° C. over $P_2O_5$.

Yield: 0.96 g (2.02 mmol) amorphous product D-20133.

The starting substance is for example obtained as follows:

27.3 g (60.0 mmol) octadecyl-2-bromoethyl phosphate are dissolved in 90 ml (900 mmol) piperidine and boiled under reflux for 1.5 hours. After cooling, the product is evaporated, the residue is dissolved in 150 ml methanol, mixed with 25.2 g (90.0 mmol) $Ag_2CO_3$ and boiled for 1.5 hours. The product is suctioned off hot over a membrane filter and evaporated. The resultant black oil is chromatographed on silica gel with $CHCl_3$/methanol/25 percent $NH_4OH$ (80:25:5). The fractions containing the octadecyl-2-piperidinoethyl phosphate are evaporated and the residue recrystallized from 200 ml butanone.

Yield: 13.2 g (28.6 mmol, 48%) Octadecyl-2-piperidinoethyl phosphate.

What is claimed is:

1. Octadecyl-[2-(N-methylpiperidino)-ethyl]-phosphate of the following formula:

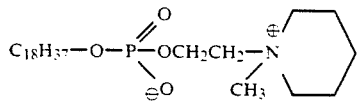

2. A pharmaceutical composition comprising octadecyl-[2-(N-methylpiperidino)-ethyl]-phosphate of claim 1 as active ingredient and pharmaceutically acceptable carriers.

* * * * *